United States Patent [19]

Chakravarty et al.

[11] Patent Number: 5,126,342
[45] Date of Patent: Jun. 30, 1992

[54] IMIDAZOLE ANGIOTENSIN II ANTAGONISTS INCORPORATING ACIDIC FUNCTIONAL GROUPS

[75] Inventors: Prasun K. Chakravarty, Edison; William J. Greenlee, Teaneck; Elizabeth M. Naylor, Scotch Plains; Arthur A. Patchett; Thomas F. Walsh, Westfield, all of N.J.

[73] Assignee: Merck & Co., Inc., Rahway, N.J.

[21] Appl. No.: 590,971

[22] Filed: Oct. 1, 1990

[51] Int. Cl.$^5$ .............. A61K 31/415; A61K 31/535; C07D 233/93; C07D 233/90

[52] U.S. Cl. .................. 514/235.8; 514/396; 514/397; 514/398; 514/399; 514/400; 544/139; 548/335; 548/336; 548/337; 548/338; 548/339; 548/340; 548/342; 548/343; 548/346

[58] Field of Search .............. 548/335, 336, 337, 339, 548/343, 346; 514/396, 398, 397, 399, 400, 235.8; 544/139

[56] References Cited

FOREIGN PATENT DOCUMENTS 253310  1/1988  European Pat. Off.
324377  7/1989  European Pat. Off.

OTHER PUBLICATIONS

Chiu et al., *Journal Pharm. Exp. Therap.*, pp. 711–718, vol. 252, No. 2, Feb. 1990.
Bolis et al., *J. Med. Chem.*, 30, 1729–1737 (1987).
Burger, A., *Medicinal Chemistry*, 2nd Ed., Interscience Pub., N.Y., pp. 565–571, 578–581, 600–601 (1960).
Denkewalter et al., *Progress in Drug Research*, vol. 10, 510–512 (1966).
Haber et al., *J. Cardiovascular Pharmacology*, 10, Suppl. S54–S58 (1987).
Plattner et al., *J. Med. Chem.*, 31, 2277–2288 (1988).

*Primary Examiner*—Patricia L. Morris
*Assistant Examiner*—Lenora Miltenberger
*Attorney, Agent, or Firm*—William H. Nicholson; Joseph F. DiPrima

[57] ABSTRACT

There are disclosed substituted imidazole derivatives of Formula I which are useful as angiotensin II antagonists.

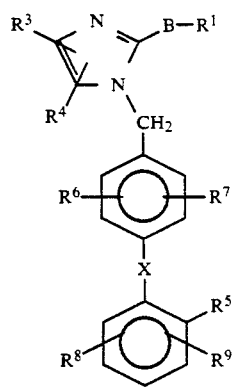

7 Claims, No Drawings

IMIDAZOLE ANGIOTENSIN II ANTAGONISTS INCORPORATING ACIDIC FUNCTIONAL GROUPS

BACKGROUND OF THE INVENTION

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; and 4,582,847 in European Patent Applications 028,834; 245,637; 253,310; and 291,969; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed in this application have been identified in any U.S. Patent, European Applications or articles. The substituted imidazoles, have been disclosed in patents to DuPont (EPO 253,310 and EPO 324,377) focusing on the design of Angiotensin II Antagonists.

BRIEF DESCRIPTION OF THE INVENTION

This invention is directed to novel substituted imidazole compounds of formula (I) which bear potentially acidic functional groups. Specifically, the compounds of this invention contain an imidazole moiety which bears substituents at the 2, 4, and 5 positions and which are substituted at the 1 position with substituted benzyl groups which, in turn, bear potentially novel acid equivalent functional groups.

The compounds of formula (I) are angiotensin II antagonists and are useful in the treatment of hypertension and congestive heart failure. Additionally, pharmaceutically acceptable compositions of these novel compounds, as the sole therapeutically active ingredient and in combination with diuretics and other antihypertensive agents, including beta-blockers, angiotensin converting enzyme inhibitors, calcium channel blockers or a combination thereof are disclosed. Further, methods of treating hypertension, congestive heart failure and elevated intraocular pressure are also described.

DETAILED DESCRIPTION OF THE INVENTION

This invention relates to compounds having the formula:

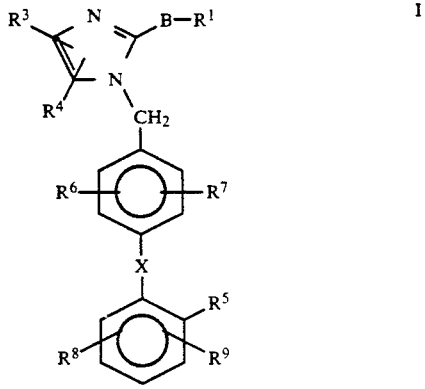

wherein:

$R^1$ is:
(a) straight chain or branched $(C_1-C_9)$-alkyl, $(C_2-C_6)$-alkenyl or $(C_2-C_6)$-alkynyl each of which can be optionally substituted with a substituent selected from the group consisting of:
  i) aryl as defined below,
  ii) $(C_3-C_7)$-cycloalkyl,
  iii) halo(Cl, Br, I, F),
  iv) $COOR^2$,
  vii) $N[((C_1-C_4)$-alkyl$)]_2$,
  viii) $NHSO_2R^2$,
  ix) $CF_3$,
  x) $COOR^2$, or
  xi) $SO_2NHR^{2a}$;
(b) aryl, wherein aryl is phenyl or naphthyl optionally substituted with 1 or 2 substituents selected from the group consisting of:
  i) halo,
  ii) $(C_1-C_4)$-alkyl,
  iii) $(C_1-C_4)$-alkoxy,
  iv) $NO_2$
  v) $CF_3$
  Vi) $SO_2NR^{2a}R^{2a}$,
  vii) $(C_1-C_4)$-alkylthio,
  viii) hydroxy,
  ix) amino,
  x) $(C_3-C_7)$-cycloalkyl,
  xi) $(C_3-C_{10})$-alkenyl;
(c) an unsubstituted, monosubstituted or disubstituted heteroaromatic 5- or 6-membered cyclic moiety, which can contain one or two members selected from the group consisting of N, O, S and wherein the substituents are members selected from the group consisting of:
  i) halo,
  ii) OH,
  iii) SH,
  iv) $NO_2$,
  v) $(C_1-C_4)$-alkyl, vi) $(C_2-C_4)$-alkenyl,
vii) $(C_2-C_4)$-alkynyl,
viii) $(C_1-C_4)$-alkoxy, or
ix) $CF_3$, or
(d) perfluoro-$(C_1-C_4)$-alkyl;

B is:
(a) a single bond,
(b) $-S(O)_x(CH_2)_s-$, or
(c) $-O-$; and x is 0 to 2,
s is 0 to 5;
m is 1 to 5;
p is 0 to 3;
n is 1 to 10;

$R^2$ is:
(a) H,
(b) straight chain $(C_1-C_6)$-alkyl, or
(c) branched chain $(C_1-C_6)$-alkyl;

$R^{2a}$ is:
(a) $R^2$,
(b) $-CH_2$-aryl as defined above, or
(c) aryl as defined above;

$R^3$ is:
(a) H,
(b) straight chain or branched $(C_1-C_6)$-alkyl, $(C_2-C_6)$-alkenyl or $(C_2-C_6)$-alkynyl,
(c) halo (Cl, Br, I, F),
(d) $NO_2$
(e) $CF_3$,
(f) $(C_1-C_8)$-perfluoroalkyl,
(g) pentafluoroethyl,
(h) CN,
(i) phenyl,
(j) phenyl-$(C_1-C_3)$-alkyl,
(k) phenyl and phenyl-$(C_1-C_3)$-alkyl substituted on the phenyl ring with one or two substituents selected from:
  i) $(C_1-C_4)$-alkyl,
  ii) $(C_1-C_4)$-alkoxyl,
  iii) halogen (F, Cl, Br, I),
  iv) hydroxyl,
  v) methoxyl,
  vi) $CF_3$,
  vii) $CO_2R^{2a}$,
  viii) $NO_2$, or
  ix) $SO_2NR^{2a}R^{2a}$;

$R^4$ is:
(a) H,
(b) CN,
(c) $(C_1-C_8)$-alkyl,
(d) $(C_3-C_6)$-alkenyl,
(e) $(C_1-C_8)$-perfluoroalkyl,
(f) $(C_2-C_8)$-perfluoroalkenyl,
(g) $CF_2CF_3$,
(h) $CO_2R^{2a}$,
(i) phenyl,
(j) phenyl-$(C_2-C_6)$-alkenyl, (k) $-\overset{O}{\underset{\|}{C}}-R^{16}$, (l) $-(CH_2)_{n-1}-\underset{\underset{R^{17}}{|}}{\overset{\overset{OR^{17}}{|}}{CH}}-R^{17}$, (m) $-(CH_2)_n-O\overset{O}{\underset{\|}{C}}R^{14}$, (n) $-(CH_2)_n-S(O)_xR^{15}$, (o) $-CH=CH(CH_2)_s-O\overset{O}{\underset{\|}{C}}R^{15}$, (p) $-CH=CH(CH_2)_s\overset{O}{\underset{\|}{C}}R^{17}$, (q) $-(CH_2)_s-\underset{\underset{O}{\|}}{\overset{\overset{CH_3}{|}}{CH}}-\overset{}{C}R^{15}$, (r) $-(CH_2)_n-\overset{O}{\underset{\|}{C}}R^{15}$, (s) $-(CH_2)_n-O\overset{O}{\underset{\|}{C}}NHR^{16}$, (t) $-(CH_2)_n-O\overset{S}{\underset{\|}{C}}NHR^{16}$, (u) $-(CH_2)_n-NHSO_2R^{16}$,
(v) $-(CH_2)_n-F$,
(w) $-(CH_2)_m$-imidazol-1-yl,
(x) $-(CH_2)_m$-1,2,3-triazolyl, optionally substituted with one or two groups selected from:
  i) $CO_2CH_3$,
  ii) $(C_1-C_4)$-alkyl,
(y) tetrazol-5-yl, (z) 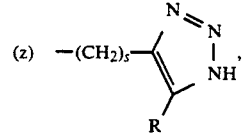, (aa) 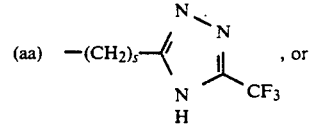, or (bb) 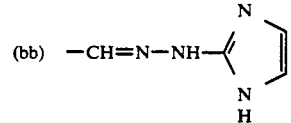

$R^5$ is
(a) $-SO_2NH$-heteroaryl,
(b) $-CH_2SO_2NH$-heteroaryl,
(c) $-SO_2NHCO-R^{12}$,
(d) $-CH_2SO_2NHCO-R^{12}$,
(e) $-CONH-SO_2NR^2R^{12}$,
(f) $-CH_2CONH-SO_2R^{12}$,
(g) $-NHSO_2NHCO-R^{12}$,
(h) $-NHCONHSO_2-R^{12}$,
(i) $-SO_2NHCONR^2R^{12}$, (j) $-\underset{\underset{OR^{11}}{|}}{\overset{\overset{O}{\|}}{P}}-R^{10}$ wherein heteroaryl is an unsubstituted, monosubstituted or disubstituted five- or six-membered aromatic ring which can optionally contain 1 to 3 heteroatoms selected from the group consisting of O, N or S and wherein the substituents are members selected from the group consisting of —OH, —SH, —$C_1$-$C_4$-alkyl, —$C_1$-$C_4$-alkoxy, halo(Cl, Br, F, I), —$NO_2$, —$CO_2H$, —$CO_2$—$C_1$-$C_4$-alkyl, —$NH_2$, —NH($C_1$-$C_4$-alkyl) and —N($C_1$-$C_4$-alkyl)$_2$;

$R^6$ is
(a) H,
(b) halo(Cl, Br, I, F)
(c) $C_1$-$C_6$-alkyl,
(d) $C_1$-$C_6$-alkoxy,
(e) $C_2$-$C_6$-alkoxyalkyl;

$R^7$ is
(a) H,
(b) halo (Cl, Br, I, F)
(c) $NO_2$,
(d) $C_1$-$C_6$-alkyl,
(e) $C_2$-$C_6$ alkanoyloxy
(f) $C_3$-$C_6$-cycloalkyl
(g) $C_1$-$C_6$-alkoxy,
(h) —$NHSO_2R^{2a}$,
(i) hydroxy $C_1$-$C_4$-alkyl,
(j) $C_1$-$C_4$-alkyl-aryl where aryl is as defined above
(k) aryl-$C_1$-$C_4$-alkyl where aryl is as defined above,
(l) $C_1$-$C_4$-alkylthio
(m) $C_1$-$C_4$-alkyl sulfinyl
(n) $C_1$-$C_4$-alkylsulfonyl
(o) $NH_2$
(p) $C_1$-$C_4$-alkylamino
(q) $C_1$-$C_4$-dialkylamino
(r) fluoro-$C_1$-$C_4$-alkyl
(s) —$SO_2$—$NHR^{10}$
(t) aryl as defined above or,
(u) furyl;

$R^8$ and $R^9$ are independently H, halo(Cl, Br, I, F), —$NO_2$, —$NH_2$, $C_1$-$C_4$-alkylamino, di($C_1$-$C_4$ alkyl)amino, —$SO_2NHR^{10}$, $CF_3$, $C_1$-$C_6$-alkyl, $C_1$-$C_6$-alkoxy, $C_2$-$C_6$-alkenyl, $C_2$-$C_6$-alkynyl or when $R^8$ and $R^9$ are on adjacent carbon atoms, they may be joined to form an aryl ring as defined above;

$R^{10}$ is H, $C_1$-$C_5$-alkyl, aryl or —$CH_2$-aryl where aryl is as defined above;

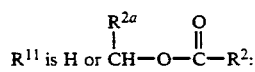

$R^{11}$ is H or CH—O—C—$R^2$:

$R^{12}$ is
(a) aryl as defined above,
(b) heteroaryl as defined above,
(c) $C_3$-$C_4$-cycloalkyl,
(d) $C_1$-$C_4$-alkyl which can be optionally substituted with a substituent that is a member selected from the group consisting of aryl as defined above, heteroaryl as defined above, —OH, —SH, —$C_1$-$C_4$-alkyl, —O($C_1$-$C_4$-alkyl), —S(-$C_1$-$C_4$-alkyl), —$CF_3$, halo(Cl, Br, F, I), —$NO_2$, —$CO_2H$, —$CO_2$—$C_1$-$C_4$-alkyl, —$NH_2$, —NH(-$C_1$-$C_4$-alkyl), —$NHCOR^{2a}$, —N($C_1$-$C_4$-alkyl)$_2$, —$PO_3H$, —PO(OH)($C_1$-$C_4$-alkyl), —PO(OH)(aryl), —PO(OH)(O—$C_1$-$C_4$-alkyl), or

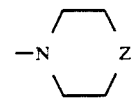

where Z is $NR^2$, O, S(O)$_x$,
(e) perfluoro-$C_1$-$C_4$-alkyl;

$R^{13}$ is:
(a) H,
(b) ($C_1$-$C_6$)-alkyl,
(c) aryl as defined above in $R^1$ (b),
(d) aryl-($C_1$-$C_6$)-alkyl-(C=O)— wherein aryl is as defined above,
(e) ($C_1$-$C_6$)-alkyl-(C=O)—,
(f) $C_3$-$C_6$-cycloalkyl,
(g) allyl;

$R^{14}$ is:
(a) H,
(b) ($C_1$-$C_8$)-alkyl,
(c) ($C_1$-$C_8$)-perfluoroalkyl,
(d) ($C_3$-$C_6$)-cycloalkyl,
(e) phenyl,
(f) benzyl;

$R^{15}$ is:
(a) H,
(b) ($C_3$-$C_6$)-alkyl,
(c) ($C_3$-$C_6$)-cycloalkyl,
(d) —(CH$_2$)$_p$-phenyl,
(e) —$OR^{17}$,
(f) morpholin-4-yl,
(g) —$NR^{18}R^{19}$;

$R^{16}$ is:
(a) ($C_1$-$C_8$)-alkyl,
(b) ($C_1$-$C_8$)-perfluoroalkyl,
(c) 1-adamantyl,
(d) 1-naphthyl,
(e) (1-naphthyl)ethyl,
(f) —(CH$_2$)$_p$-phenyl;

$R^{17}$ is:
(a) H,
(b) ($C_1$-$C_6$)-alkyl,
(c) ($C_3$-$C_6$)-cycloalkyl,
(d) phenyl,
(e) benzyl;

$R^{18}$ and $R^{19}$ are independently:
(a) H,
(b) ($C_1$-$C_4$)-alkyl,
(c) phenyl,
(d) benzyl,
(e) α-methylbenzyl;

$R^{20}$ is:
(a) H,
(b) $C_1$-$C_6$-alkyl,
(c) $C_3$-$C_6$-cycloalkyl,
(d) —$CH_2$-aryl where aryl is as defined above;

X is absent or is
(a) a carbon-carbon single bond,
(b) —$CH_2$—,
(c) —CO—,
(d) —O—,
(e) —S(O)$_x$—, (f) —N—
      |
      $R^{13}$ (g) —N—CH₂,
     |
     R¹³

(h) —CH₂—N
         |
         R¹³

(i) —CON—,
      |
      R²⁰

(j) —NCO—,
      |
      R²⁰

(k) —OCH₂—,
(l) —CH₂O—
(m) —S(O)$_x$—CH₂—,
(n) —CH₂S(O)$_x$—,
(o) —NHC(R¹⁰)(R²⁰),
(p) —NR¹⁰SO₂—,
(q) —SO₂NR¹⁰—,
(r) —C(R¹⁰)(R²⁰)NH—,
(s) —CH=CH—,
(t) —CF=CF—,
(u) —CH=CF—,
(v) —CF=CH—,
(w) —CH₂CH₂—,
(x) —CF₂CF₂—, (y) 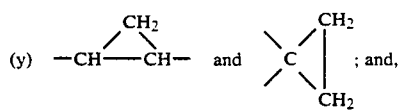 ; and, the pharmaceutically acceptable salts thereof.

One embodiment of the compounds of Formula I or those wherein:

R¹ is:
(a) straight chain or branched (C₁-C₉)-alkyl, (C₂-C₆)-alkenyl or (C₂-C₆)-alkynyl each of which can be optionally substituted with a substituent selected from the group consisting of:
  i) aryl as defined below,
  ii) (C₃-C₇)-cycloalkyl,
  iii) halo(Cl, Br, I, F), or
  iv) CF₃;
(b) perfluoro-(C₁-C₄)-alkyl;

B is:
a single bond or —S—;

R³ is:
(a) H,
(b) straight chain or branched (C₁-C₆)-alkyl, (C₂-C₆)-alkenyl or (C₂-C₆)-alkynyl,
(c) halo (Cl, Br, I, F),
(d) NO₂
(e) CF₃,
(f) (C₁-C₈)-perfluoroalkyl,
(g) pentafluorophenyl,
(h) CN,
(i) phenyl,
(j) phenyl-(C₁-C₃)-alkyl,
(k) phenyl and phenyl-(C₁-C₃)-alkyl substituted on the phenyl ring with one or two substituents selected from:
  i) (C₁-C₄)-alkyl,
  ii) (C₁-C₄)-alkoxyl,
  iii) halogen (F, Cl, Br, I),
  iv) hydroxyl,
  v) methoxyl,
  vi) CF₃, or
  vii) CO₂R²ᵃ;

R⁴ is:
(a) H,
(b) CN,
(c) (C₁-C₈)-alkyl,
(d) (C₃-C₆)-alkenyl,
(e) (C₁-C₈)-perfluoroalkyl,
(f) (C₂-C₈)-perfluoroalkenyl,
(g) CF₂CF₃,
(h) CO₂R²ᵃ,
(i) phenyl,
(j) phenyl-(C₂-C₆)-alkenyl, (k) 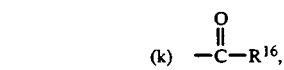

(l) 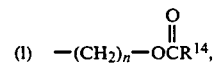

(m) —(CH₂)$_n$—SO₂R¹⁵ where n is 0–4,
(n) —(CH₂)$_m$-1,2,3-triazolyl, optionally substituted with one or two groups selected from:
  i) CO₂CH₃,
  ii) (C₁-C₄)-alkyl,
(o) tetrazol-5-yl, or (p) 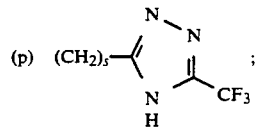

R⁵ is:
(a) —SO₂NH-heteroaryl,
(b) —CH₂SO₂NH-heteroaryl,
(c) —SO₂NHCO—R¹²,
(d) —CH₂SO₂NHCO—R¹²,
(e) —CONH—SO₂NR²R¹²,
(f) —CH₂CONH—SO₂R¹²,
(g) —NHSO₂NHCO—R¹²,
(h) —NHCONHSO₂—R¹²,
(i) —SO₂NHCONR²R¹², (j) 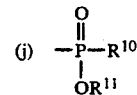

wherein heteroaryl is as defined above; and,
X is a carbon-carbon single bond.

Illustrative of this embodiment are the following compounds:

(1) 1-[(2'-((Benzoylamino)sulfonyl)(1,1'-biphenyl)-4-yl)methyl]-2-butyl-4-chloro-5-hydroxymethyl-imidazole;

(2) 1-[(2'-((Benzoylamino)sulfonyl)(1,1'-biphenyl)-4-yl)methyl]-2-butyl-4-chloro-5-methoxymethyl-imidazole;

(3) 1-[(2-((Benzoylamino)sulfonyl)(1,1'-biphenyl)-4-yl)methyl]-2-butyl-5-carbomethoxy-4-chloro-imidazole;

(4) 1-[(2'-((Benzoylamino)sulfonyl)(1,1'-biphenyl)-4-yl)methyl]-2-butyl-5-carboxymethyl-4-chloro-imidazole;

(5) 1-[(2'-((Benzoylamino)sulfonyl)(1,1'-biphenyl)-4-yl)methyl]-2-butyl-4-chloro-imidazole-5-carboxylic acid;

(6) 1-[(2'-((Benzoylamino)sulfonyl)(1,1'-biphenyl)-4-yl)methyl]-2-butyl-5-hydroxymethyl-4-phenyl-imidazole;

(7) 1-[(2'-((Benzoylamino)sulfonyl)(1,1'-biphenyl)-4-yl)methyl]-2-butyl-5-methoxymethyl-4-phenyl-imidazole;

(8) 1-[(2'-((Benzoylamino)sulfonyl)(1,1'-biphenyl)-4-yl)methyl]-2-butyl-5-carboxymethyl-4-phenyl-imidazole;

(9) 1-[(2'-((Benzoylamino)sulfonyl)(1,1'-biphenyl)-4-yl)methyl]-5-carbomethoxy-4-chloro-2-propyl-imidazole;

(10) 1-[(2'-((Benzoylamino)sulfonyl)(1,1'-biphenyl)-4-yl)methyl]-2-butyl-4-phenyl-imidazole-5-carboxylic acid;

(11) 1-[(2'-((Benzoylamino)sulfonyl)(1,1'-biphenyl)-4-yl)methyl]-2-butyl-4-trifluoromethyl-imidazole-5-carboxylic acid;

(12) 1-[(2'-((Benzoylamino)sulfonyl)(1,1'-biphenyl)-4-yl)methyl]-2-butyl-5-hydroxymethyl-4-trifluoromethyl-imidazole;

(13) 1-[(2'-((Benzoylamino)sulfonyl)(1,1'-biphenyl)-4-yl)methyl]-2-butyl-5-carbomethoxy-4-trifluoromethylimidazole;

(14) 1-[(2'-((Benzoylamino)sulfonyl)(1,1'-biphenyl)-4-yl)methyl]-2-butyl-5-carboxymethyl-4-trifluoromethylimidazole;

(15) 1-[(2'-((Benzoylamino)sulfonyl)(1,1'-biphenyl)-4-yl)methyl]-2-butyl-4-pentafluoroethyl-imidazole-5-carboxylic acid;

(16) 1-[(2'-((Benzoylamino)sulfonyl)(1,1'-biphenyl)-4-yl)methyl]-2-butyl-5-hydroxymethyl-4-pentafluoroethylimidazole;

(17) 1-[(2'-((Benzoylamino)sulfonyl)(1,1'-biphenyl)-4-yl)methyl]-2-butyl-5-carbomethoxy-4-pentafluoromethylimidazole;

(18) 1-[(2'-((Benzoylamino)sulfonyl)(1,1'-biphenyl)-4-yl)methyl]-2-butyl-5-carboxymethyl-4-pentafluoroethylimidazole;

(19) 1-[(2'-((Benzoylamino)sulfonyl)(1,1'-biphenyl)-4-yl)methyl]-2-butyl-5-methoxymethyl-4-pentafluoroethylimidazole;

(20) 1-[(2'-((4-Nitrobenzoylamino)sulfonyl)(1,1'-biphenyl)-4-yl)methyl]-2-butyl-5-hydroxymethyl-4-pentafluoroethylimidazole;

(21) 1-[(2'-((2Nitrobenzoylamino)sulfonyl)(1,1'-biphenyl)-4-yl)methyl]-2-butyl-5-hydroxymethyl-4-pentafluoroethylimidazole;

(22) 1-[(2'-((4-Bromobenzoylamino)sulfonyl)(1,1'-biphenyl)-4-yl)methyl]-2-butyl-5-hydroxymethyl-4-pentafluoroethylimidazole;

(23) 1-[(2'-((2-Bromobenzoylamino)sulfonyl)(1,1'-biphenyl)-4-yl)methyl]-2-butyl-5-hydroxymethyl-4-pentafluoroethylimidazole;

(24) 1-[(2'-((3-Chlorobenzoylamino)sulfonyl)(1,1'-biphenyl)-4-yl)methyl]-2-butyl-5-hydroxymethyl-4-pentafluoroethylimidazole;

(25) 1-[(2'-((4-Fluorobenzoylamino)sulfonyl)(1,1'-biphenyl)-4-yl)methyl]-2-butyl-5-hydroxymethyl-4-pentafluoroethylimidazole;

(26) 1-[(2'-((2-Fluorobenzoylamino)sulfonyl)(1,1'-biphenyl)-4-yl)methyl]-2-butyl-5-hydroxymethyl-4-pentafluoroethylimidazole;

(27) 1-[(2'-((3-Fluorobenzoylamino)sulfonyl)(1,1'-biphenyl)-4-yl)methyl]-2-butyl-5-hydroxymethyl-4-pentafluoroethylimidazole;

(28) 1-[(2'-((4-Nitrobenzoylamino)sulfonyl)(1,1'-biphenyl)-4-yl)methyl]-2-butyl-4-trifluoromethyl-imidazole-5-carboxylic acid;

(29) 1-[(2'-((2-Nitrobenzoylamino)sulfonyl)(1,1'-biphenyl)-4-yl)methyl]-2-butyl-4-trifluoromrethyl-imidazole-5-carboxylic acid;

(30) 1-[(2'-((3-Nitrobenzoylamino)sulfonyl)(1,1'-biphenyl)-4-yl)methyl]-2-butyl-4-trifluoromethyl-imidazole-5-carboxylic acid;

(31) 1-[(2'-((4-Chlorobenzoylamino)sulfonyl)(1,1'-biphenyl)-4-yl)methyl]-2-butyl-4-trifluoromethyl-imidazole-5-carboxylic acid;

(32) 1-[(2'-((2-Chlorobenzoylamino)sulfonyl)(1,1'-biphenyl)-4-yl)methyl]-2-butyl-4-trifluoromethyl-imidazole-5-carboxylic acid;

(33) 1-[(2'-((3-Chlorobenzoylamino)sulfonyl)(1,1'-biphenyl)-4-yl)methyl]-2-butyl-4-trifluoromethyl-imidazole-5-carboxylic acid;

(34) 1-[(2'-Dichlorobenzoylamino)sulfonyl)(1,1'-biphenyl)-4-yl)methyl]-2-butyl-4-trifluoromethyl-imidazole-5-carboxylic acid;

(35) 1-[(2'-((3,4-Dichlorobenzoylamino)sulfonyl)(1,1'-biphenyl)-4-yl)methyl]-2-butyl-4-trifluoromethyl-imidazole-5-carboxylic acid;

(36) 1-[(2'-((4-Fluorobenzoylamino)sulfonyl)(1,1'-biphenyl)-4-yl)methyl]-2-butyl-4-trifluoromethyl-imidazole-5-carboxylic acid;

(37) 1-[(2'-((2-Fluorobenzoylamino)sulfonyl)(1,1'-biphenyl)-4-yl)methyl]-2-butyl-4-trifluoromethyl-imidazole-5-carboxylic acid;

(38) 1-[(2'-((3-Fluorobenzoylamino)sulfonyl)(1,1'-biphenyl)-4-yl)methyl]-2-butyl-4-trifluoromethyl-imidazole-5-carboxylic acid;

(39) 1-[(2'-((2,4-Difluorobenzoylamino)sulfonyl)(1,1'-biphenyl)-4-yl)methyl]-2-butyl-4-trifluoromethyl-imidazole-5-carboxylic acid;

(40) 1-[(2'-((3,4-Difluorobenzoylamino)sulfonyl)(1,1'-biphenyl)-4-yl)methyl]-2-butyl-4-trifluoromethyl-imidazole-5-carboxylic acid;

(41) 1-[(2'-((4-Bromobenzoylamino)sulfonyl)(1,1'-biphenyl)-4-yl)methyl]-2-butyl-4-trifluoromethyl-imidazole-5-carboxylic acid;

(42) 1-[(2'-((2-Bromobenzoylamino)sulfonyl)(1,1'-biphenyl)-4-yl)methyl]-2-butyl-4-trifluoromethyl-imidazole-5-carboxylic acid; and

(43) 1-[(2'-((4-Nitrobenzoylamino)sulfonyl)(1,1'-biphenyl)-4-yl)methyl]-2-butyl-4-pentafluoroethyl-imidazole-5-carboxylic acid.

GENERAL METHODS FOR PREPARATION OF COMPOUNDS OF GENERAL FORMULA I

The methods described below illustrate the preparation of angiotensin II antagonists of Formula I. There are several general approaches to the synthesis of antagonists of Formula I, and it is taken as a general principle that one or another method may be more readily applicable for the preparation of a given antagonist; some of the approaches illustrated below may not be readily applicable for the preparation of certain antagonists of Formula I.

Abreviations used in the following schemes and examples are listed below:

| Reagents | |
|---|---|
| NBS | N-bromosuccinimide |
| AIBN | Azo(bis)isobutyronitrile |
| Ac₂O | acetic anhydride |
| TEA | triethylamine |
| DMAP | 4-dimethylaminopyridine |
| PPh₃ | triphenylphosphine |
| TFA | trifluoroacetic acid |
| TMS-Cl | trimethylsilyl chloride |
| p-TsOH | p-toluenesulfonic acid |
| DIPEA | Diisopropylethylamine |
| TBAF | tetrabutylammonium fluoride |
| Solvents | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Others: | |
| rt | room temperature |
| TBDMS | t-butyldimethylsilyl |
| OTf | OSO₂CF₃ |
| Ph | phenyl |
| FAB-MS (FSBMS) | Fast atom bombardment mass spectroscopy |
| NOE | Nuclear Overhauser Effect |
| SiO₂ | silica gel |
| trityl | triphenylmethyl |

As shown in Scheme 1, compounds of Formula I can be prepared by carrying out direct alkylation of alkalimetal salts of imidazole derivatives (1) (preparation of imidazole derivatives are described in European Patent Applications 253,310 and 324,377 which are incorporated herein by reference thereto) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with a metal alkoxide such as sodium or potassium methoxide, ethoxide or t-butoxide in an appropriate alcohol such as methanol, ethanol or t-butanol as the solvent. The alkylation is generally carried out by dissolving the metal salt of the heterocycle in a dipolar aprotic solvent such as DMF or dimethylsulfoxide (DMSO) and reacting it with the alkylating agent at 20° C. to reflux temperature of the solvent for 1-24 hours.

SCHEME 1

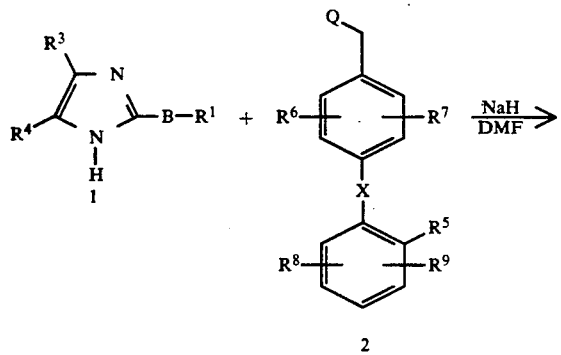

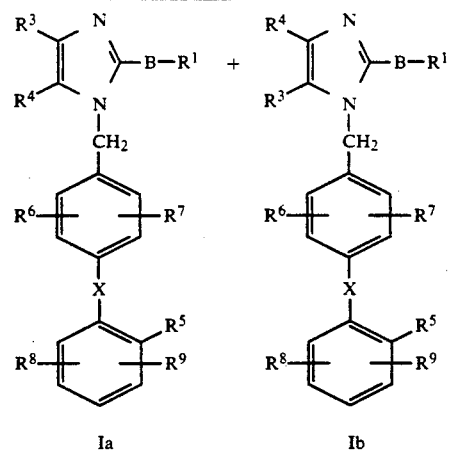

where Q = halo(I, Br, Cl), —O-tosyl, —O-mesyl

If substituents on the imidazole ring are not symmetrically disposed, the alkylation on the imidazole nitrogen(s) generally produces a mixture of two regioisomers as products arising from $N^1$ and $N^3$ alkylation. These regioisomers Ia and Ib possess distinct physicochemical and biological properties and in most cases can be separated and purified by using conventional separation techniques such as chromatography (flash column chromatography, medium-pressure liquid chromatography, high performance liquid chromatography) and/or crystallization. In thoses cases where separation of regioisomers is difficult by conventional techniques, the mixture can be transformed into suitable derivatives that can be separated by the above separation methods. The structural assignments of the isomers can be made using Nuclear Overhauser Effect (NOE), $^1H—^{13}C$ coupled NMR experiments or X-ray crystallography.

The biphenyl precursors 7a, 7b and 7c required for the synthesis of substituted benzyl halides (2) may be preferably prepared using Ni(O) or Pd(O) catalyzed cross-coupling reaction [E. Negishi, T. Takahashi, and A. O. King, Org. Synthesis, 66, 67 (1987)] as is outlined in Scheme 2. As shown in Scheme 2, treatment of 4-bromotoluene (3) with t-BuLi, followed by the addition of a solution of ZnCl₂, produces the organo-zinc compound (5). Compound (5) is then coupled with 6a, 6b or 6c in the presence of Pd(PPh₃)₄ or Ni(PPh₃)Cl₂ catalyst to produce the desired biphenyl compound 7a, 7b or 7c, respectively. These precursors (7a, 7b and 7c) are then transformed into bromomethylbiphenyl derivatives 8a, 8b and 8c, respectively, by reacting them with N-bromosuccinimide in the presence of AlBN in refluxing carbontetrachloride.

When there are additional substituents on the second phenyl ring ($R^8$ and $R^9$ are not hydrogen) the preferred method to prepare the biphenyl precursors 11 using Pd(O) catalyzed cross-coupling reaction [J. K. Stille, Angew, Chem. Int. Ed. Engl., 25, 508 (1986)], is outlined in Scheme 3. As shown in Scheme 3, p-tolyltrimethyltin (9) is reacted with 10 in refluxing toluene in the presence of 5 mole % of Pd(PPh₃)₄ or in dry DMF in the presence of Pd(PPh₃)₂Cl₂ at 90° C. to produce the desired biphenyl compounds 11. Compounds 11 bearing $R^8$ or $R^9$ as NO₂ groups could be converted to their respective chlorides by catalytic hydrogenation, diazotization and treatment with copper (I) chloride. Similarly, the biphenyl fluorides which could not be obtained by direct coupling to a fluoroarylbromide precursor (10) were prepared from the corresponding nitro compound via reduction, formation of the diazonium tetrafluoroborate salt and thermal decomposition. These precursors 11 are then transformed into the halomethyl biphenyl derivatives 12 according to the procedures described in European Patent Applications 253,310 and 292,969.

SCHEME 2

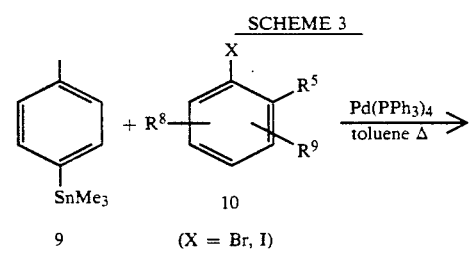

SCHEME 3

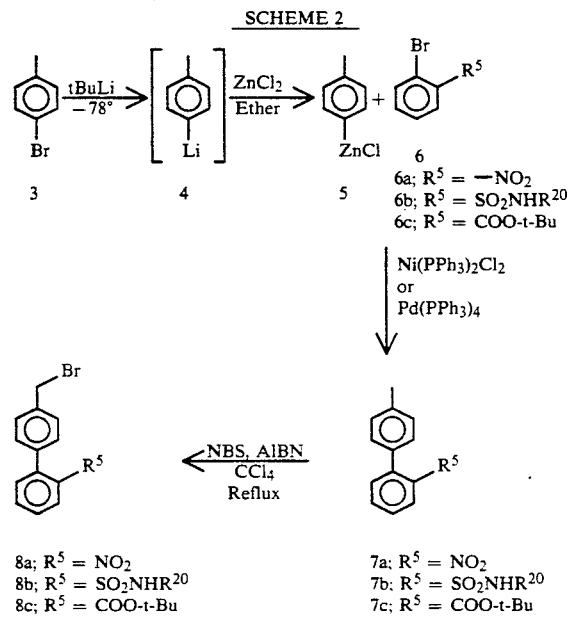

-continued
SCHEME 3

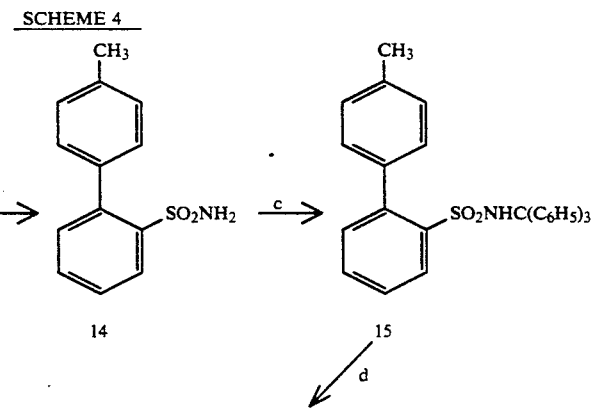

Compounds of formula I where $R^5$ is —$SO_2NH$-$COR^{12}$ may be prepared as outlined in Scheme 4. The nitro compound 7a (prepared as described in Scheme 2) can be reduced to the corresponding amino compound and converted into aromatic diazonium chloride salt, which then can be reacted with sulfur-dioxide in the presence of a copper(I) salt to form the corresponding arylsulfonylchloride 13 [H. Meerwein, G. Dittmar, R. Gollner, K. Hafner, F. Mensch and O. Steifort—*Chem. Ber.*, 90, 841 (1957); A. J. Prinsen and H. Cerfontain, Recueil, 84, 24 (1965); E. E. Gilbert, *Synthesis*, 3 (1969) and references cited therein]. The sulfonyl chloride can be reacted with ammonia in aqueous solution or in an inert organic solvent [F. H. Bergheim and W. Baker, *J. Amer. Chem. Soc.*, 66, (1944), 1459], or with dry powdered ammonium carbonate, [E. H. Huntress and J. S. Autenrieth, *J. Amer. Chem. Soc.*, 63, (1941), 3446; E. H. Huntress and F. H. Carten, *J. Amer. Chem. Soc.*, 62, (1940), 511] to form the sulfonamide 14. The benzylbromide 16 may be prepared from the sulfonamide 14 as outlined in Scheme 4, and then can be reacted with an alkali metal salt of an appropriate imidazole derivative to form the key sulfonamide 17. The sulfonamide 17 may be also prepared from the aromatic sulfonyl chloride 22, which may be prepared from the aryl amine 21 as outlined in Scheme 5. The acylation of 17 with appropriate acyl chlorides (or acyl-imidazoles or other acylating agents) may produce the desired acylsulfonamides 18.

SCHEME 4

SCHEME 4

-continued

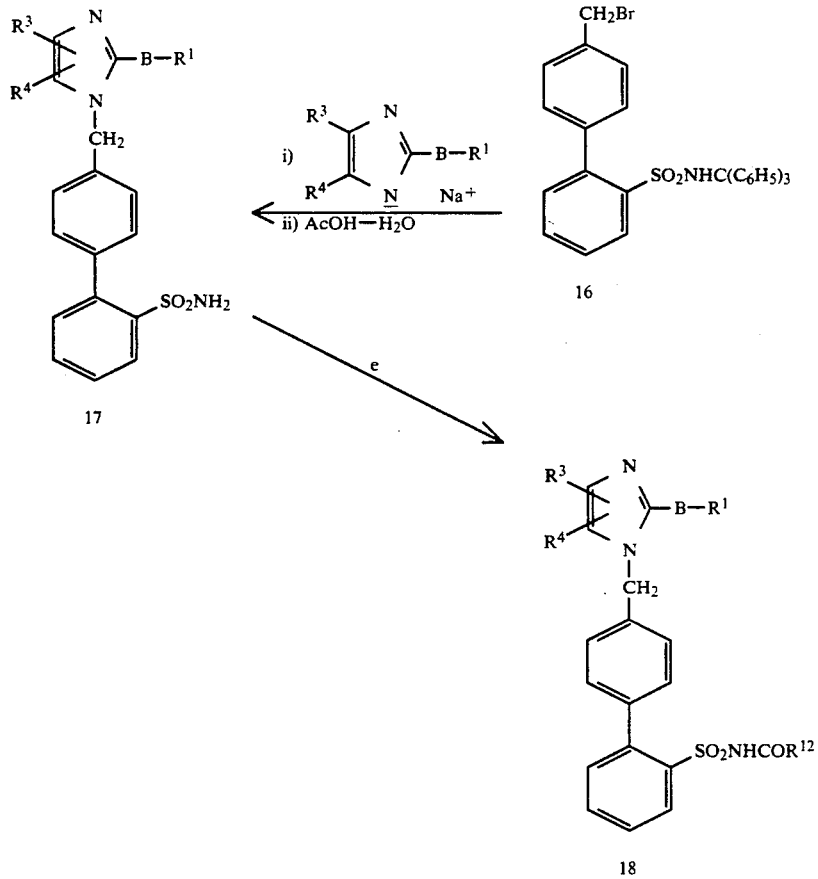

a. i) H₂/Pd—C, ii) NaNO₂—HCl, iii) SO₂, AcOH, CuCl₂
b. NH₃ or (NH₄)₂CO₃
c. (C₆H₅)₃CCl, Et₃N, CH₂Cl₂, 25° C.
d. N-Bromosuccinimide
e. R¹²COCl or R¹²CO—Im or other acylating agents.

The compounds (23) bearing $R^5$ as —SO₂NHR¹² (where $R^{12}$ is heteroaryl) may be prepared by reacting the aromatic sulfonyl chloride 22 with appropriate heteroaryl amines as outlined in Scheme 5. The sulfonyl chloride 22 may be prefered intermediate for the synthesis of this class of compounds. The aromatic sulfonyl chlorides may also be prepared by reacting the sodium salt of aromatic sulfonic acids with PCl₅ or POCl₃ [C. M. Suter, *The organic Chemistry of Sulfur*, John Wiley & sons, 459, (1944)]. The aromatic sulfonic acid precursors may be prepared by chlorosulfonation of the aromatic ring with chlorosulfonic acid [E. H. Huntress and F. H. Carten, *J. Amer. Chem. Soc.*, 62, 511 (1940)].

SCHEME 5

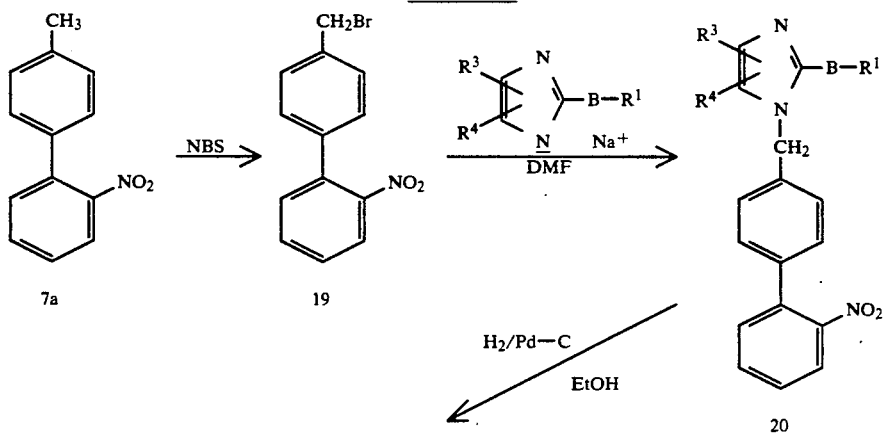

SCHEME 5
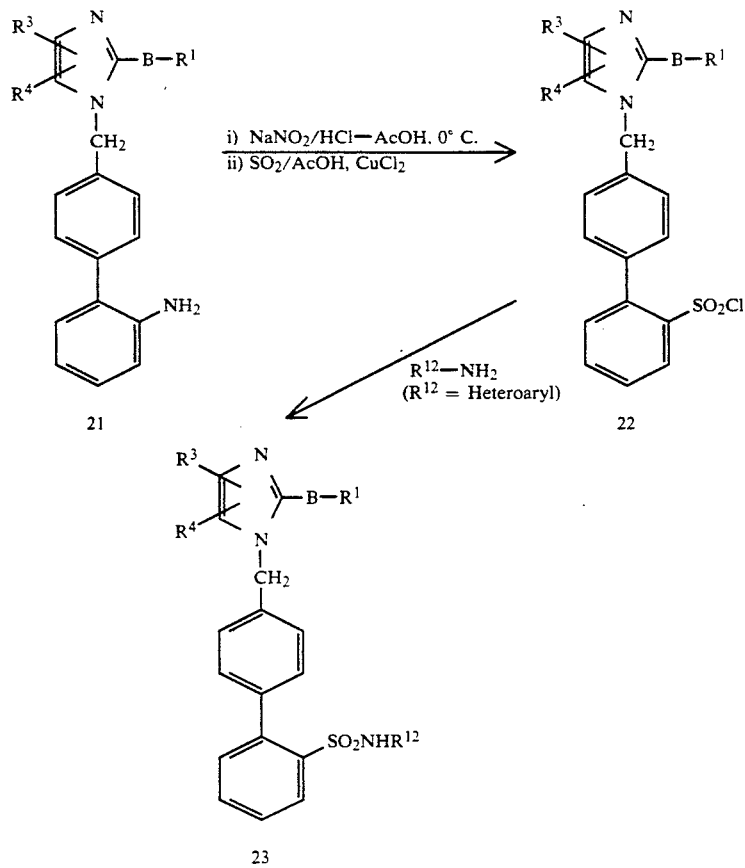
SCHEME 6
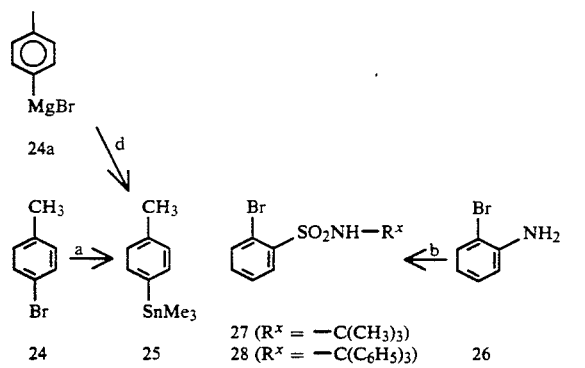
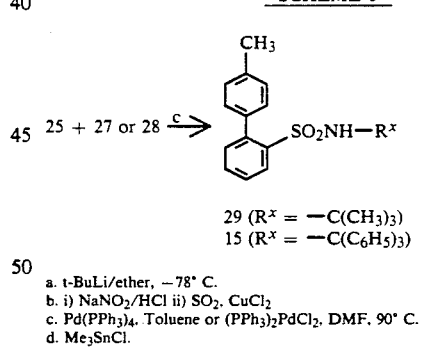
a. t-BuLi/ether, −78° C.
b. i) NaNO$_2$/HCl ii) SO$_2$, CuCl$_2$
c. Pd(PPh$_3$)$_4$, Toluene or (PPh$_3$)$_2$PdCl$_2$, DMF, 90° C.
d. Me$_3$SnCl.
SCHEME 7
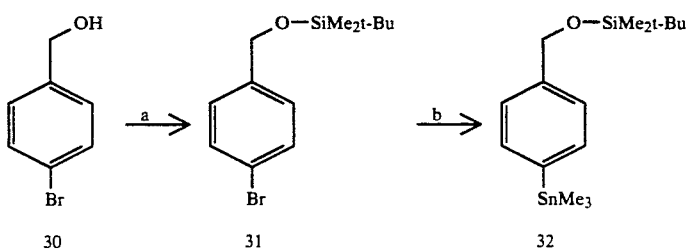

SCHEME 7
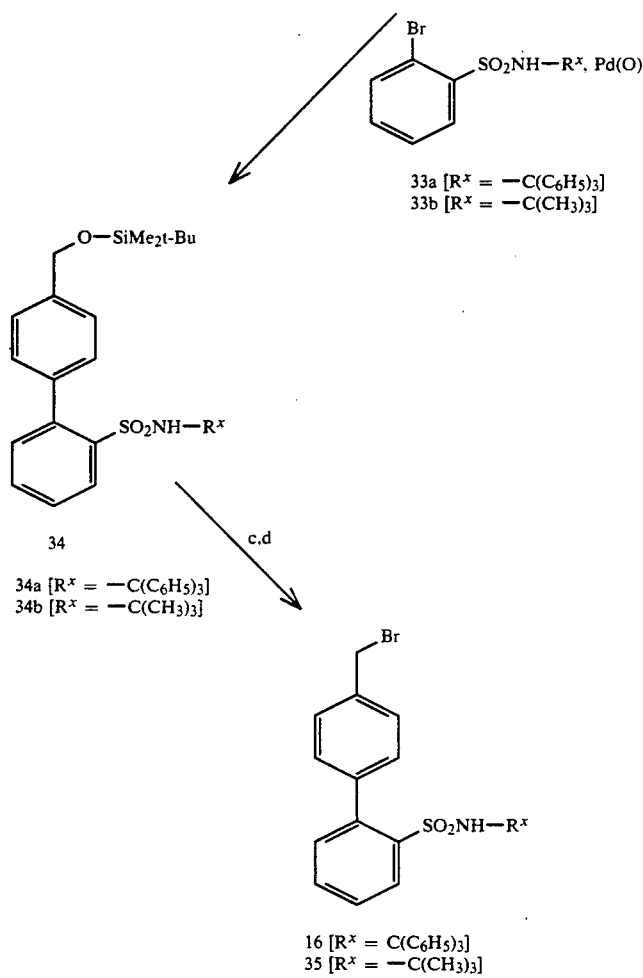
a. t-BuMe₂Si—Cl/Imidazole, DMF
b. t-BuLi, −78° C., Me₃SnCl
c. Tetrabutylammonium fluoride
d. CBr₄/Ph₃P.
SCHEME 8
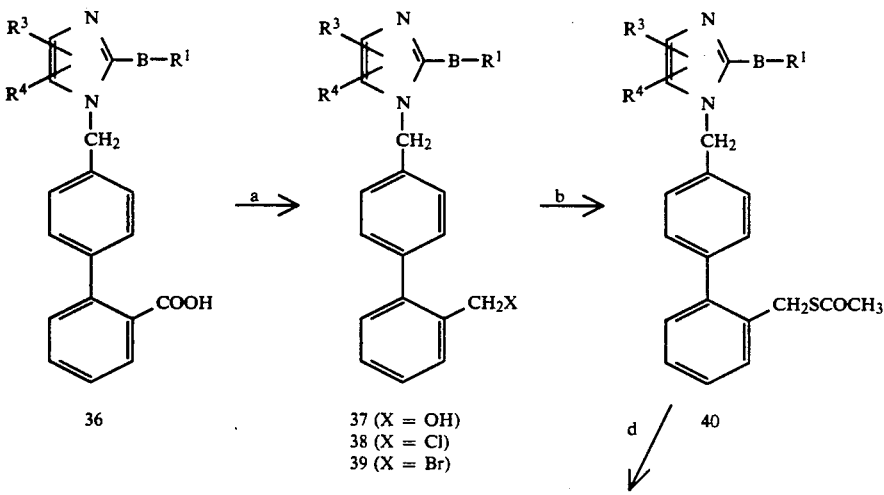

-continued
SCHEME 8
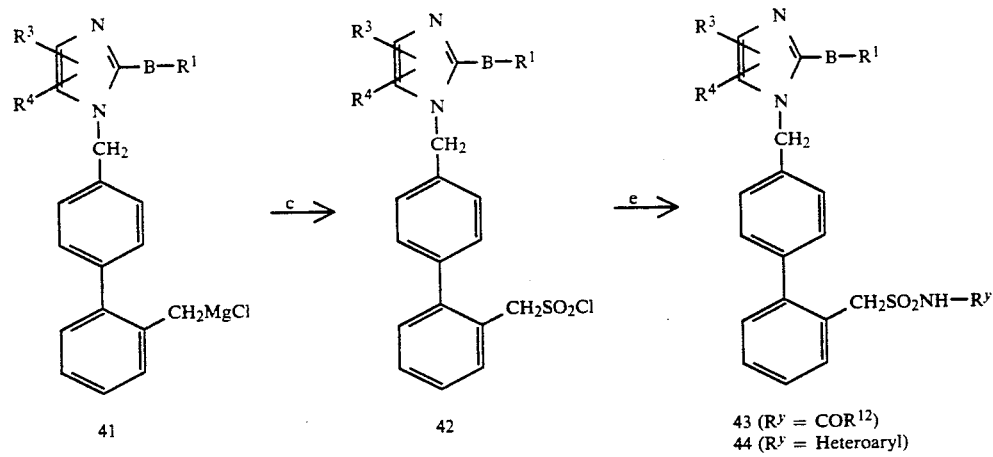
a. i) EtOCOCl/Et₃N, THF, 0° C.
   ii) NaBH₄
   iii) CCl₄ or CBr₄/PPh₃
b. AcSK
c. SO₂Cl₂
d. Cl₂, AcOH, H₂O or,
   i) SO₂Cl₂
   ii) oxidation
e. R$^y$NH₂ or,
   i) NH₃
   ii) Acylation
SCHEME 9

SCHEME 10
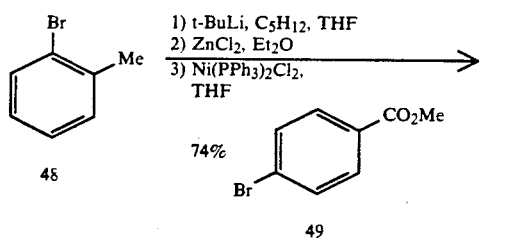
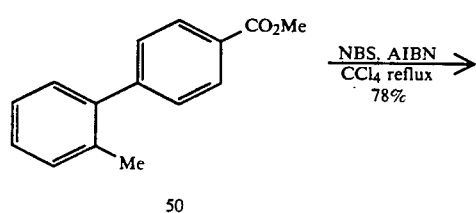
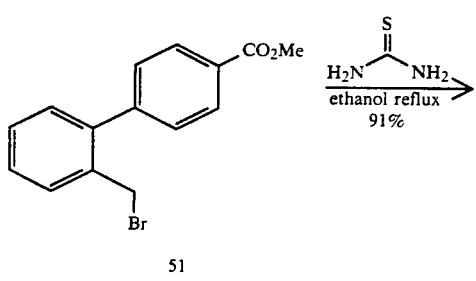
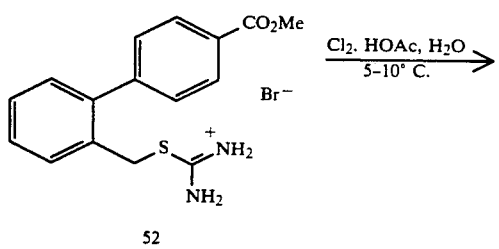
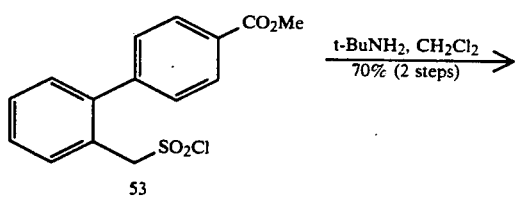
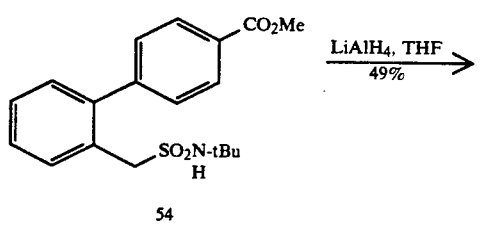
-continued
SCHEME 10
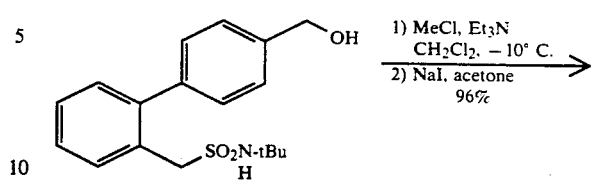
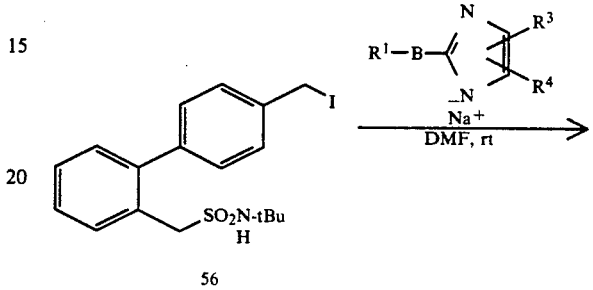
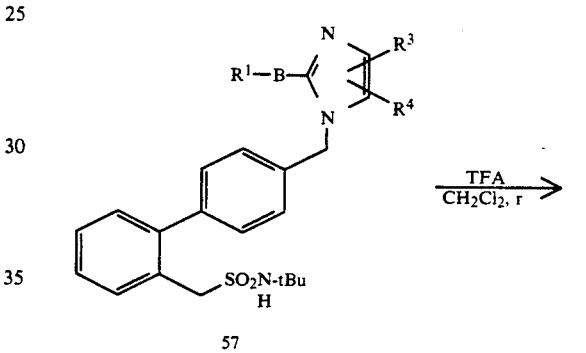
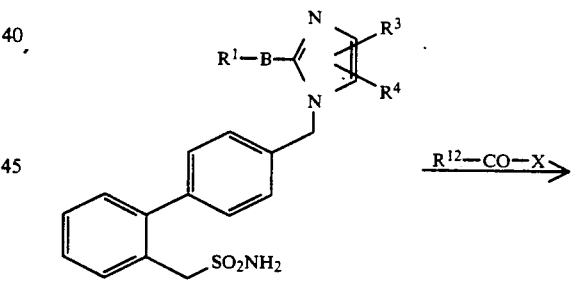
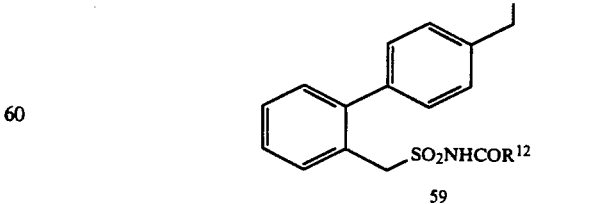
The biaryl sulfonamides 29 and 15 can be prepared alternatively using palladium(O) catalyzed cross-coupling reactions of appropriate aryl-organotin precursors [J. K. Stille, *Pure Appl. Chem.*, 57, 1771 (1985); T. R.

Bailey, *Tetra Lett.*, 27, 4407 (1986); D. A. Widdowson and Y. Z. Zhang, *Tetrahedron*, 42, 2111 (1986)], as outlined in Scheme 6. The organotin compound 25 [S. M. Moerlein, *J. Organometallic Chem.*, 319, 29 (1987)], obtained from the aromatic precursor 24 or 24a, may be coupled with aryl sulfonamides 27 and 28 using Pd(PPh$_3$)$_4$ or (PPh$_3$)$_2$PdCl$_2$ as catalysts to give biaryl sulfonamides 29 and 15, respectively. Similarly, the benzyl bromides 16 and 35 may be alternatively prepared from the appropriate organotin precursor 32 using the Pd(O) catalyzed cross-coupling reaction as outlined in Scheme 7.

The compounds bearing $R^5$ as —CH$_2$SO$_2$NHCOR$^{12}$ and —CH$_2$SO$_2$NHR$^{12}$ may be prepared as outlined in Scheme 8. The key precursor aryl-methanesulfonyl chloride 42 may be prepared either from the reaction of aryl-methylmagnesium chloride (41) (obtained from the corresponding benzyl chloride (38)) with sulfurylchloride [S. N. Bhattacharya, C. Eaborn and D. P. M. Walton, *J. Chem. Soc.* C, 1265 (1968)], or by oxidation of the aryl-methylthioacetate (40) (prepared from the benzyl bromide 39) with chlorine in presence of trace amount of water [Bagnay and Dransch, *Chem. Ber.*, 93, 784 (1960)]. Alternatively, the aryl-methylthioacetate (40) may be oxidized with sulfuryl chloride in presence of acetic anhydride to form aryl-methylsulfinyl chloride [S. Thea and G. Cevasco, *Tetra. Lett.*, 28, 5193 (1987)], which can be further oxidized with appropriate oxidizing agents to give the sulfonyl chloride 42. The compounds 43 and 44 can be obtained by reacting the sulfonyl chloride 42 with appropriate amines or with ammonia followed by acylation.

Compounds where $R^5$=—NHSO$_2$NHR$^{12}$ may be prepared by the reaction of appropriate primary amines with the sulfamide 46 [S. D. McDermott and W. J. Spillane, *Synthesis*, 192 (1983)], as described in Scheme 9. The compound 46 may be obtained from the corresponding N-t-butylsulfamide 45 after treatment with anhydrous trifluoroacetic acid [J. D. Catt and W. L. Matier, *J. Org. Chem.*, 39, 566 (1974)], which may be prepared by the reaction of the aromatic amine 21 with t-butylsulfamoyl chloride [W. L. Matier, W. T. Comer and D. Deitchman, *J. Med. Chem.*, 15, 538 (1972)].

Antagonists of Formula I in which $R^5$=—CH$_2$SO$_2$NHCOR$^{12}$ may be prepared as illustrated in Scheme 10. 2-Bromotoluene (48) is treated with t-butyllithium and then zinc chloride. Coupling of the resulting metallo-zinc species with 4-bromobenzoic acid methyl ester (49) is then carried out with bis(triphenylphosphine)nickle(II) chloride as catalyst. Bromination of the resulting biphenyl (50) is then carried out using N-bromosuccinimide, affording bromide 51. Treatment of the bromide with thiourea affords the salt 52 which is treated with chlorine to yield sulfonyl chloride 53. Treatment of 53 with t-butylamine affords sulfonamide 54, which is converted by treatment with lithium aluminum hydride to the alcohol 55. Conversion of 55 to the corresponding iodide 56 is carried out by treatment with methanesulfonyl chloride to afford a sulfonate ester, followed by treatment with sodium iodide in acetone. The iodide 56 is used to alkylate the sodium salt of an appropriate heterocyclic compound, affording the sulfonamide 57. Treatment of 57 with trifluoroacetic acid then affords the sulfonamide analog 58, which on further treatment with an appropriate acylating agent affords the desired acylsulfonamides 59.

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H$_2$SO$_4$, H$_3$PO$_4$, methane-sulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor Binding Assay Using Rabbit Aortae Membrane Preparation

Three frozen rabbit aortae (obtained from Pel-Freeze Biologicals) were suspended in 5 mM Tris-0.25M Sucrose, pH 7.4 buffer (50 ml) homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM MgCl$_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 ul; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC$_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor Assay Using Bovine Adrenal Cortex Preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there was added 3H-angiotensin II (50 mM) (10 ul) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^3H$-angiotensin II was presented as a measure of the efficacy of such compounds as AII antagonists.

Using the methodology described above, representative compounds of the invention were evaluated and were found to exhibit an activity of at least $IC_{50} < 50$ μM thereby demonstrating and confirming the utility of the compounds of the invention as effective AII antagonists.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.). The trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minutes, volumn—1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered and 15 minutes later propranolol (1 mg/kg i.v.). Thirty minutes later antagonists of formula I were administered intravenously or orally. Angiotensin II was then typically given at 5, 10, 15, 30, 45 and 60 minute intervals and every half-hour thereafter for as long as the test compound showed activity. The change in the mean arterial blood pressure was recorded for each angiotensin II challenge and the percent inhibition of the angiotensin II response was calculated.

Thus, the compounds of the invention are useful in treating hypertension. They are also of value in the management of acute and chronic congestive heart failure.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, *rauwolfia serpentina*, rescinnamine, reserpine, sodium nitroprusside, spironolactone, timolol maleate, trichloromethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5–250 milligrams per day range can be effectively combined at levels at the 0.5–250 milligrams per day range with the following compounds at the indicated per day dose range: hydrochlorothiazide (15–200 mg) chlorothiazide (125–2000 mg), ethacrynic acid (15–200 mg), amiloride (5–20 mg), furosemide (5–80 mg), propanolol (20–480 mg), timolol maleate (5–60 mg.), methyldopa (65–2000 mg), felodipine (5–60 mg), nifedipine (5–60 mg), and nitrendipine (5–60 mg). In addition, triple drug combinations of hydrochlorothiazide (15–200 mg) plus amiloride (5–20 mg) plus angiotensin II antagonist of this invention (3–200 mg) or hydrochlorothiazide (15-200 mg) plus timolol maleate (5-60) plus an angiotensin II antagonists of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, thsee dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, aracia, corn starch or gelatin; an excipient such as microcrystalline cellulose; a distintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of Formula I and their incorporation into pharmaceutical compositions and as such are not to be considered nor construed as limiting the invention set forth in the claims appended hereto.

EXAMPLE 1

Preparation of
1-((2'-((benzoylamino)sulfonyl)(1,1'-biphenyl)-4-yl)methyl)-2-butyl-4-chloro-1H-imidazole-5-carboxylic acid Step 1: Preparation of
2-bromobenzene(tert-butyl)sulfonamide To a stirred solution of 2-bromobenzenesulfonyl chloride (Lancaster Synthesis) (2.21 g, 8.65 mmol) in chloroform (40 ml) under nitrogen at room temperature was added tert-butylamine (Aldrich) (2.30 ml, 21.9 mmol). The orange solution was stirred at room temperature for 12 hours, then the mixture evaporated to dryness. Flash chromatography (silica gel, 15% ethyl acetate-hexane) afforded 2-bromobenzene(tert-butyl)sulfonamide (2.12 g, 84%) as a white solid; $^1$H NMR (300 MHz, CDCl$_3$) δ8.18 (d, J=8.5 Hz, 1H), 7.73 (d, J=8.5 Hz, 1H), 7.50-7.35 (m, 2H), 5.11 (s, 1H), 1.20 (s, 9H).

Step 2: Preparation of p-tolyltrimethyltin p-Tolylmagnesium bromide solution (Aldrich) (1.0M solution in diethyl ether) (53 ml, 0.0530 mol) was added dropwise to trimethyltin chloride (6.92 g, 0.0347 mol) in tetrahydrofuran (50 ml) under nitrogen at −10° C. The suspension was allowed to warm slowly to room temperature over 3 hours then saturated ammonium chloride solution (10 ml) was added followed by sufficient water to dissolve the precipitate. The solution was extracted three times with diethyl ether-hexane (1:1). The combined organic phase was washed with brine, dried (magnesium sulfate) and the solvents removed in vacuo. Vacuum distillation of the residue afforded a colorless liquid (39°-40° C., 0.1 mm Hg) which was further purified by flash chromatography (silica gel, hexane) to give p-tolyltrimethyltin (7.30 g, 82%) as a colorless liquid; $^1$H NMR (300 MHz, CDCl$_3$) δ7.40 (d, J=7.7 Hz, 2H), 7.19 (d, J=7.7 Hz, 2H), 2.34 (s, 3H), 0.30 (s, 9H).

Step 3: Preparation of
4'-methylbiphenyl-2-tert-butylsulfonamide

2-Bromobenzene(tert-butyl)sulfonamide (1.00 g, 3.92 mmol), p-tolyl-trimethyltin (1.95 g, 6.67 mmol), bis(triphenylphosphine)palladiumII chloride (Aldrich) (165 mg, 0.235 mmol) and dimethylformamide (25 ml) were heated with stirring under nitrogen at 90° C. for 5 hours. The black suspension was cooled to room temperature, then filtered through a pad of celite which was washed with tetrahydrofuran. The colorless filtrate was evaporated to dryness then chromatographed (silica gel, 10% ethyl acetate-hexane) to give 4'-methylbiphenyl-2-tert-butylsulfonamide (0.88 g, 74%) as a white solid; $^1$H NMR (300 MHz, CDCl$_3$) δ8.16 (d, J=7.9 Hz, 1H), 7.60-7.37 (m, 4H), 7.36-7.24 (m, 3H), 3.57 (s, 1H), 2.42 (s, 3H), 0.99 (s, 9H).

Step 4: Preparation of
4'-bromomethylbiphenyl-2-tert-butylsulfonamide

N-Bromosuccinimide (387 mg, 2.17 mmol), α,α'-azoisobutytonitrile (catalytic), 4'-methylbiphenyl-2-tert-butylsulfonamide (550 mg, 1.81 mmol) and carbon tetrachloride (50 ml) were heated with stirring at reflux for 3 hour. After cooling to room temperature the mixture was filtered and the filtrate evaporated to dryness. Flash chromatography (silica gel, initially 10 and then 20% ethyl acetate-hexane) afforded 4'-bromo-methylbiphenyl-2-tert-butylsulfonamide (699 mg, 77% pure (the remainder of the material was 4'-dibromomethylbiphenyl-2-tert-butylsulfonamide), 97% as a white solid; $^1$H NMR (300 MHz, CDCl$_3$) δ8.17 (dd, J=7.5, 1.6 Hz, 1H), 7.68-7.45 (m, 6H), 7.31 (dd, J=7.5, 1.6 Hz, 1H), 4.55 (s, 2H), 3.52 (s, 1H), 1.00 (s, 9H).

Step 5: Preparation of
1-((2'-((tert-butylamino)sulfonyl)(1,1'-biphenyl)-4-yl)methyl)-2-butyl-4-chloro-1H-imidazole-5-carboxylic acid, methyl ester To a stirred solution of 2-butyl-4-chloro-1H-imidazole-5-carboxylic acid, methyl ester (150 mg, 0.692 mmol) in dimethylformamide (10 ml) under nitrogen at room temperature was added potassium carbonate (143 mg, 1.03 mmol). The mixture was heated at 100° C. for 0.5 hours then cooled to room temperature.

4'-Bromomethylbiphenyl-2-tert-butylsulfonamide (393 mg, 74% pure, 0.761 mmol) was added and stirring continued at room temperature for 12 hours. The solvent was removed in vacuo then the residue partitioned between ethyl acetate and water. The organic phase was separated and the aqueous phase re-extracted three times with ethyl acetate. The combined organic phase was washed with brine, dried (magnesium sulfate) and the solvent removed in vacuo. Flash chromatography (silica gel, initially 25 and then 50% ethyl acetate-hexane) afforded two isomers, isomer A:

1-((2'-tert-butylamino)sulfonyl)(1,1'-biphenyl)-4-yl)methyl)-2-butyl-4-chloro-1H-imidazole-5-carboxylic acid, methyl ester, recrystallised from ethyl acetate-hexane, (197 mg, 55%) as white needles;

$^1$H NMR (300 MHz, CD$_3$OD) δ8.10 (d, J=7.7 Hz, 1H), 7.61 (t, J=7.7 Hz, 1H), 7.52 (t, J=7.7 Hz, 1H), 7.45 (d, J=8.1 Hz, 2H), 7.31 (d, J=7.7 Hz, 1H), 7.11 (d, J=8.1 Hz, 2H), 5.70 (s, 2H), 3.82 (s, 3H), 2.74 (t, J=7.4 Hz, 2H), 1.65 (quin, J=7.4 Hz, 2H), 1.35 (m, 2H), 1.00 (s, 9H), 0.92 (t, J=7.4 Hz, 3H);

isomer B:

1-((2'-((tert-butylamino)sulfonyl)(1,1'-biphenyl)-4-yl)methyl)-2-butyl-5-chloro-1H-imidazole-4-carboxylic acid, methyl ester (55 mg, 15%) as a white solid;

$^1$H NMR (300 MHz, CD$_3$OD) δ8.11 (d, J=7.7 Hz, 1H), 7.60 (t, J=7.7 Hz, 1H), 7.55-7.45 (m, 3H), 7.30 (d, J=7.7 Hz, 1H), 7.15 (d, J=8.1 Hz, 2H), 5.39 (s, 2H), 3.88 (s, 3H), 2.72 (t, J=7.4 Hz, 2H), 1.61 (quin, J=7.4 Hz, 2H), 1.35 (sext, J=7.4 Hz, 2H), 1.01 (s, 9H), 0.90 (t, J=7.4 Hz, 3H).

Step 6: Preparation of 1-((2'-(aminosulfonyl)(1,1'-biphenyl)-4-yl)methyl)-2-butyl-4-chloro-1H-imidazole-5-carboxylic acid, methyl ester 1-((2'-((tert-butylamino)sulfonyl)(1,1'-biphenyl)-4-yl)methyl)-2-butyl-4-chloro-1H-imidazole-5-carboxylic acid, methyl ester (75.0 mg, 0.145 mmol) was stirred in trifluoroacetic acid (1.0 ml) containing anisole (20 μl) under nitrogen at room temperature for 24 hours. The trifluoroacetic acid was removed in vacuo and the residue chromatographed (silica gel, 35% ethyl acetate-hexane) to afford 1-((2'-aminosulfonyl)(1,1'-biphenyl)-4-yl)methyl)-2-butyl-4-chloro-1H-imidazole-5-carboxylic acid, methyl ester (67.5 mg, 100%) as a white solid; $^1$H NMR (300 MHz, CD$_3$OD/CDCl$_3$) δ8.08 (d, J=7.7 Hz, 1H), 7.54 (t, J=7.7 Hz, 1H), 7.46 (t, J=7.7 Hz, 1H), 7.40 (d, J=8.1 Hz, 2H), 7.26 (d, J=7.7 Hz, 1H), 7.04 (d, J=8.1 Hz, 2H), 5.57 (s, 2H), 3.80 (s, 3H), 2.64 (t, J=7.4 Hz, 2H), 1.62 (quin, J=7.4 Hz, 2H), 1.31 (sext, J=7.4 Hz, 2H), 0.89 (t, J=7.4 Hz, 3H).

Step 7: Preparation of 1-((2'-((benzoylamino)sulfonyl)(1,1'-biphenyl)-4-yl)methyl)-2-butyl-4-chloro-1H-imidazole-5-carboxylic acid, methyl ester To a stirred solution of 1-((2'-(aminosulfonyl)(1,1'-biphenyl)-4-yl)methyl)-2-butyl-4-chloro-1H-imidazole-5-carboxylic acid, methyl ester (67.0 mg, 0.145 mmol) in pyridine (1.0 ml) under nitrogen at room temperature was added benzoyl chloride (168 μl, 1.45 mmol) dropwise. The pale orange solution was stirred at room temperature for 12 hours then saturated sodium bicarbonate solution added. The mixture was extracted four times with ethyl acetate. The compound organic phase was washed with water, twice with saturated copper sulfate solution, water, brine and dried (magnesium sulfate). The solvent was removed in vacuo and the residue chromatographed (silica gel, 2% methanol-methylene chloride) to give 1-((2'-((benzylamino)sulfonyl)(1,1'-biphenyl)-4-yl)methyl)-2-butyl-4-chloro-1H-imidazole-5-carboxylic acid, methyl ester (63.4 mg, 77%) as a white solid; $^1$H NMR (300 MHz, CD$_3$OD) δ8.30 (dd, J=7.7, 1.7 Hz, 1H), 7.65-7.42 (m, 5H), 7.40-7.30 (m, 2H), 7.29-7.18 (m, 3H), 6.90 (d, J=8.2 Hz, 2H), 5.54 (s, 2H), 3.84 (s, 3H), 2.62 (t, J=7.8 Hz, 2H), 1.64 (quin, J=7.8 Hz, 2H), 1.32 (apparent sext, 2H), 0.87 (t, J=7.3 Hz, 3H); FAB-MS: 568 and 566 (M+H).

Step 8: Preparation of 1-((2'-((benzoylamino)sulfonyl)(1,1'-biphenyl)-4-yl)methyl)-2-butyl-4-chloro-1H-imidazole-5-carboxylic acid To a stirred suspension of 1-((2'-((benzoylamino)sulfonyl)(1,1'-biphenyl)-4-yl)methyl)-2-butyl-4-chloro-1H-imidazole-5-carboxylic acid, methyl ester (25 mg, 0.044 mmol) in methanol (1.0 ml) was added 2N sodium hydroxide solution (0.50 ml). The pale yellow solution was stirred at room temperature for 3 hours then the methanol was removed in vacuo. Saturated sodium dihydrogen phosphate solution was added followed by ethyl acetate and the organic phase separated. The aqueous phase was re-extracted twice with ethyl acetate, then the combined organic phase washed with brine, dried, (magnesium sulfate) and the solvent removed in vacuo. Flash chromatography (silica gel, 0.25% acetic acid-2.5% methanolmethylene chloride) afforded 1-((2'-((benzoylamino)sulfonyl)(1,1'-biphenyl)-4-yl)methyl)-2-butyl-4-chloro-1H-imidazole-5-carboxylic acid (11.5 mg, 47%) as a white solid; $^1$H NMR (300 MHz, CD$_3$OD) δ8.27 (d, J=8.5 Hz, 1H), 7.71-7.50 (m, 3H), 7.50-7.36 (m, 4H), 7.35-7.23 (m, 3H), 6.98 (d, J=8.0 Hz, 2H), 5.70 (s, 2H), 2.67 (apparent t, 2H), 1.64 (apparent quin, 2H), 1.35 (apparent sext, 2H), 0.90 (t, J=7.3 Hz, 3H); FAB-MS: 574 (M+Na), 552 (M+H).

EXAMPLE 2

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| 1-((2'-((benzoylamino)sulfonyl)-(1,1'-biphenyl)-4-yl)methyl)-2-butyl-4-chloro-1H-imidazole-5-carboxylic acid | 50 |
| Lactose | 149 |
| Magnesium stearate | 1 |
| Capsule (size No. 1) | 200 |

The 1-((2'-benzoylamino)sulfonyl)(1,1'-biphenyl)-4-yl)methyl)-2-butyl-4-chloro-1H-imidazole-5-carboxylic acid can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B. Tablet

A typical tablet would contain 1-((2'-((benzoylamino)sulfonyl)(1,1'-biphenyl)-4-yl)methyl)-2-butyl-4-chloro-1H-imidazole-5-carboxylic acid (25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide and consist of 1-((2'-((benzoylamino)sulfonyl)(1,1'-biphenyl)-4-yl)methyl)-2-butyl-4-chloro-1H-imidazole-5-carboxylic acid (50 mg) pregelatinized starch USP (82 mg), microcrystalline cellulose (82 mg) and magnesium stearate (1 mg).

D: Suppository

Typical suppository formulations for rectal administration can contain 1-((2'-((benzoylamino)sulfonyl)(1,1'-biphenyl)-4-yl)methyl)-2-butyl-4-chloro-1H-imidazole-5-carboxylic acid (0.08-1.0 mg), disodium calcium edetate (0.25-0.5 mg), and polyethylene glycol (775-1600 mg). Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like for the polyethylene glycol. Further, these suppository formulations can also include another active ingredient such as another antihypertensive and/or a diuretic and/or an angiotensin converting enzyme inhibitor and/or a calcium channel blocker in pharmaceutically effective amounts as described, for example, in C above.

E: Injection

A typical injectible formulation would contain 1-((2'-benzoylamino)sulfonyl)(1,1'-biphenyl)-4-yl)methyl)-2-butyl-4-chloro-1H-imidazole-5-carboxylic acid sodium phosphate dibasic anhydrous (11.4 mg) benzyl alcohol (0.01 ml) and water for injection (1.0 ml). Such as injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of structural formula

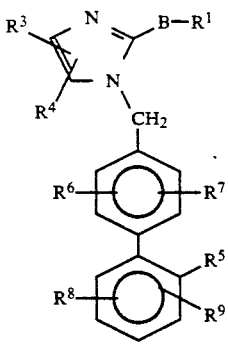

or a pharmaceutically acceptable salt thereof, wherein:
$R^1$ is:
(a) straight chain or branched $(C_1-C_9)$-alkyl, $(C_2-C_6)$-alkenyl or $(C_2-C_6)$-alkynyl each of which can be optionally substituted with a substituent selected from the group consisting of:
i) aryl as defined below,
ii) $(C_3-C_7)$-cycloalkyl,
iii) halo,
iv) $COOR^2$,
v) $N[((C_1-C_4)\text{-alkyl})]_2$,
vi) $NHSO_2R^2$,
vii) $CF_3$, and
viii) $SO_2NHR^{2a}$; or
(b) perfluoro-$(C_1-C_4)$-alkyl wherein aryl is phenyl or naphthyl optionally substituted with 1 or 2 substituents selected from the group consisting of:
i) halo,
ii) $(C_1-C_4)$-alkyl,
iii) $(C_1-C_4)$-alkoxy,
iv) $NO_2$,
v) $CF_3$,
vi) $SO_2NR^{2a}R^{2a}$,
vii) $(C_1-C_4)$-alkylthio,
viii) hydroxy,
ix) amino,
x) $(C_3-C_7)$-cycloalkyl, or
xi) $(C_3-C_{10})$-alkenyl;
B is:
(a) a single bond,
(b) —S—, or
(c) —O—;
$R^2$ is:
(a) H,
(b) $(C_1-C_6)$-alkyl;
$R^{2a}$ is:
(a) $R^2$,
(b) —$CH_2$-aryl wherein aryl is as defined above, or
(c) aryl as defined above;
$R^3$ is:
(a) H,
(b) $(C_1-C_6)$-alkyl, $(C_2-C_6)$-alkenyl or $(C_2-C_6)$-alkynyl,
(c) halo,
(d) $NO_2$,
(e) $(C_1-C_8)$-perfluoroalkyl,
(f) pentafluorophenyl,
(g) CN,
(h) phenyl,
(i) phenyl-$(C_1-C_3)$-alkyl, or
(j) phenyl or phenyl-$(C_1-C_3)$-alkyl each substituted on the phenyl ring with one or two substituents selected from:
i) $(C_1-C_4)$-alkyl,
ii) $(C_1-C_4)$-alkoxyl,
iii) halo,
iv) hydroxyl,
v) methoxyl,
vi) $CF_3$,
vii) $CO_2R^{2a}$,
viii) $NO_2$, and
ix) $SO_2NR^{2a}R^{2a}$;
$R^4$ is:
(a) H,
(b) CN,
(c) $(C_1-C_8)$-alkyl,
(d) $(C_3-C_6)$-alkenyl,
(e) $(C_1-C_8)$-perfluoroalkyl,
(f) $(C_2-C_8)$-perfluoroalkenyl,
(g) $CO_2R^{2a}$,
(h) phenyl,
(i) phenyl-$(2-C_6)$-alkenyl,

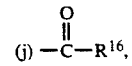

-continued (k) $-(CH_2)_{n-1}-\underset{\underset{OR^{17}}{|}}{CH}-R^{17}$, (l) $-(CH_2)_n-O\overset{O}{\underset{\|}{C}}R^{14}$, (m) $-(CH_2)_n-S(O)_xR^{15}$, (n) $-CH=CH(CH_2)_s-O\overset{O}{\underset{\|}{C}}R^{15}$, (o) $-CH=CH(CH_2)_s-\overset{O}{\underset{\|}{C}}R^{17}$, (p) $-(CH_2)_s-\underset{\underset{CH_3}{|}}{CH}-\overset{O}{\underset{\|}{C}}R^{15}$, (q) $-(CH_2)_n-\overset{O}{\underset{\|}{C}}R^{15}$, (r) $-(CH_2)_n-O\overset{O}{\underset{\|}{C}}NHR^{16}$, (s) $-(CH_2)_n-O\overset{S}{\underset{\|}{C}}NHR^{16}$, (t) $-(CH_2)_n-NHSO_2R^{16}$, or
(u) $-(CH_2)_n-F$;

$R^5$ is:
(a) $-SO_2NHCO-R^{12}$,
(b) $-CH_2SO_2NHCO-R^{12}$,
(c) $-CONH-SO_2NR^2R^{12}$,
(d) $-CH_2CONH-SO_2R^{12}$,
(e) $-NHSO_2NHCO-R^{12}$,
(f) $-NHCONHSO_2-R^{12}$, or
(g) $-SO_2NHCONR^2R^{12}$;

$R^6$ is:
(a) H,
(b) halo,
(c) $(C_1-C_6)$-alkyl,
(d) $(C_1-C_6)$-alkoxy, or
(e) $(C_2-C_6)$-alkoxyalkyl;

$R^7$ is:
(a) H,
(b) halo,
(c) $NO_2$,
(d) $(C_1-C_6)$-alkyl,
(e) $(C_2-C_6)$-alkanoyloxy,
(f) $(C_3-C_6)$-cycloalkyl,
(g) $(C_1-C_6)$-alkoxy,
(h) $-NHSO_2R^{2a}$,
(i) hydroxy $(C_1-C_4)$-alkyl,
(j) $(C_1-C_4)$-alkyl-aryl where aryl is as defined above,
(k) aryl-$(C_1-C_4)$-alkyl where aryl is as defined above,
(l) $(C_1-C_4)$-alkylthio,
(m) $(C_1-C_4)$-alkylsulfinyl,
(n) $(C_1-C_4)$-alkylsulfonyl,
(o) $NH_2$,
(p) $(C_1-C_4)$-alkylamino,
(q) di($(C_1-C_4)$-alkyl)amino,
(r) fluoro-$(C_1-C_4)$-alkyl,
(s) $-SO_2-NHR^{10}$,
(t) aryl as defined above or,
(u) furyl;

$R^8$ and $R^9$ are independently H, halo, $-NO_2$, $-NH_2$, $C_1-C_4$-alkylamino, di(($C_1-C_4$)-alkyl)amino, $-SO_2NHR^{10}$, $CF_3$, $(C_1-C_6)$-alkyl, $(C_1-C_6)$-alkoxy, $(C_2-C_6)$-alkenyl, $(C_2-C_6)$-alkynyl or when $R^8$ and $R^9$ are one adjacent carbon atoms, they may be joined to form an aryl ring as defined above;

$R^{10}$ is:
H, $C_1-C_5$-alkyl, aryl or $-CH_2$-aryl where aryl is as defined above;

$R^{12}$ is:
(a) aryl as defined above,
(b) $(C_3-C_4)$-cycloalkyl,
(c) $(C_1-C_8)$-alkyl which can be optionally substituted with a substituent that is a member selected from the group consisting of aryl as defined above, $-OH$, $-SH$, $-O(C_1-C_4)$-alkyl, $-S(-C_1-C_4)$-alkyl, $-CF_3$, halo, $-NO_2$, $-CO_2H$, $-CO_2-(C_1-C_4)$-alkyl, $-NH_2$, $-NH(C_1-C_4)$-alkyl, $-NHCOR^{2a}$, and $-N((C_1-C_4)$-alkyl)$_2$, or
(d) perfluoro-$(C_1-C_4)$-alkyl;

$R^{14}$ is:
(a) H,
(b) $(C_1-C_8)$-alkyl,
(c) $(C_1-C_8)$-perfluoroalkyl,
(d) $(C_3-C_6)$-cycloalkyl,
(e) phenyl, or
(f) benzyl;

$R^{15}$ is:
(a) H,
(b) $(C_1-C_6)$-alkyl,
(c) $(C_3-C_6)$-cycloalkyl,
(d) $-(CH_2)_p$-phenyl,
(e) $-OR^{17}$,
(f) morpholin-4-yl, or
(g) $-NR^{18}R^{19}$;

$R^{16}$ is:
(a) $(C_1-C_8)$-alkyl,
(b) $(C_1-C_8)$-perfluoroalkyl,
(c) 1-adamantyl,
(d) 1-naphthyl,
(e) (1-naphthyl)ethyl, or
(f) $-(CH_2)_p$-phenyl;

$R^{17}$ is:
(a) H,
(b) $(C_1-C_6)$-alkyl,
(c) $(C_3-C_6)$-cycloalkyl,
(d) phenyl, or
(e) benzyl;

$R^{18}$ and $R^{19}$ are independently:
(a) H,
(b) $(C_1-C_4)$-alkyl,
(c) phenyl,
(d) benzyl, or
(e) a-methylbenzyl;

x is 0 to 2;
s is 0 to 5;
p is 0 to 3; and
n is 1 to 10.

2. The compound of claim 1 wherein:
$R^1$ is:
(a) $(C_1-C_9)$-alkyl, $(C_2-C_6)$alkenyl or $(C_2-C_6)$-alkynyl each of which can be optionally substituted with a substituent selected from the group consisting of:
i) aryl, ii) (C$_3$–C$_7$)-cycloalkyl,
iii) halo, or
iv) CF$_3$;
(b) perfluoro-(C$_1$–C$_4$)-alkyl;

B is:
a single bond or —S—;

R$^3$ is:
(a) H,
(b) (C$_1$–C$_6$)-alkyl, (C$_2$–C$_6$)-alkenyl or (C$_2$–C$_6$)-alkynyl,
(c) halo,
(d) NO$_2$,
(e) (C$_1$–C$_8$)-perfluoroalkyl,
(f) pentafluorophenyl,
(g) phenyl,
(h) phenyl-(C$_1$–C$_3$)-alkyl,
(j) phenyl or phenyl-(C$_1$–C$_3$)-alkyl substituted on the phenyl ring with one or two substituents selected from:
  i) (C$_1$–C$_4$)-alkyl,
  ii) (C$_1$–C$_4$)-alkoxyl,
  iii) halo,
  iv) hydroxyl,
  v) methoxyl;
  vi) CF$_3$, and
  vii) CO$_2$R$^{2a}$;

R$^4$ is:
(a) H,
(b) CN,
(c) (C$_1$–C$_8$)-alkyl,
(d) (C$_3$–C$_6$)-alkenyl,
(e) (C$_1$–C$_8$)-perfluoroalkyl,
(f) (C$_2$–C$_8$)-perfluoroalkenyl,
(g) CO$_2$R$^{2a}$,
(h) phenyl,
(i) phenyl-(C$_2$–C$_6$)-alkenyl,

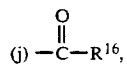

(j) —C—R$^{16}$,

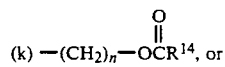

(k) —(CH$_2$)$_n$—OCR$^{14}$, or (l) —(CH$_2$)$_n$—SO$_2$R$^{15}$ where n is 0–4; and R$^5$ is
(a) —SO$_2$NHCO—R$^{12}$,
(b) —CH$_2$SO$_2$NHCO—R$^{12}$,
(c) —CONH—SO$_2$NR$^2$R$^{12}$,
(d) —CH$_2$CONH—SO$_2$R$^{12}$,
(e) —NHSO$_2$NHCO—R$^{12}$,
(f) —NHCONHSO$_2$—R$^{12}$, or
(g) —SO$_2$NHCONR$^2$R$^{12}$.

3. The compound of claim 2 which is a member of the group:

(1) 1-[(2'-((Benzoylamino)sulfonyl)(1,1'-biphenyl)-4-yl)methyl]-2-butyl-4-chloro-5-hydroxymethyl-imidazole;
(2) 1-[(2'-((Benzoylamino)sulfonyl)(1,1'-biphenyl)-4-yl)methyl]-2-butyl-4-chloro-imidazole-5-carboxylic acid;
(3) 1-[(2'-((Benzoylamino)sulfonyl)(1,1'-biphenyl)-4-yl)methyl]-2-butyl-4-phenyl-imidazole-5-carboxylic acid;
(4) 1-[(2'-((Benzoylamino)sulfonyl)(1,1'-biphenyl)-4-yl)methyl]-2-butyl-4-trifluoromethyl-imidazole-5-carboxylic acid;
(5) 1-[(2'-((Benzoylamino)sulfonyl)(1,1'-biphenyl)-4-yl)methyl]-2-butyl-4-pentafluoroethyl-imidazole-5-carboxylic acid;
(6) 1-[(2'-((4-Nitrobenzoylamino)sulfonyl)(1,1'-biphenyl)-4-yl)methyl]-2-butyl-4-trifluoromethyl-imidazole-5-carboxylic acid;
(7) 1-[(2'-((2-Nitrobenzoylamino)sulfonyl)(1,1'-biphenyl)-4-yl)methyl]-2-butyl-4-trifluoromethyl-imidazole-5-carboxylic acid;
(8) 1-[(2'-((2-Chlorobenzoylamino)sulfonyl)(1,1'-biphenyl)-4-yl)methyl]-2-butyl-4-trifluoromethyl-imidazole-5-carboxylic acid;
(9) 1-[(2'-((2,4-Dichlorobenzoylamino)sulfonyl)(1,1'-biphenyl)-4-yl)methyl]-2-butyl-4-trifluoromethyl-imidazole-5-carboxylic acid;
(10) 1-[(2'-((4-Fluorobenzoylamino)sulfonyl)(1,1'-biphenyl)-4-yl)methyl]-2-butyl-4-trifluoromethyl-imidazole-5-carboxylic acid;
(11) 1-[(2'-((2-Fluorobenzoylamino)sulfonyl)(1,1'-biphenyl)-4-yl)methyl]-2-butyl-4-trifluoromethyl-imidazole-5-carboxylic acid;
(12) 1-[(2'-((2,4-Difluorobenzoylamino)sulfonyl)(1,1'-biphenyl)-4-yl)methyl]-2-butyl-4-trifluoromethyl-imidazole-5-carboxylic acid;
(13) 1-[(2'-((2-Bromobenzoylamino)sulfonyl)(1,1'-biphenyl)-4-yl)methyl]-2-butyl-4-trifluoromethyl-imidazole-5-carboxylic acid; and,
(14) 1-[(2'-((4-Nitrobenzoylamino)sulfonyl)(1,1'-biphenyl)-4-yl)methyl]-2-butyl-4-pentafluoroethyl-imidazole-5-carboxylic acid.

4. A pharmaceutical composition useful in the treatment of hypertension which comprises a pharmaceutically acceptable carrier and a pharmaceutically effective amount of a compound of claim 1.

5. A method of treating hypertension which comprises administering to a patient in need of such treatment a pharmaceutically effective amount of a compound of claim 1.

6. An ophthalmological formulation for the treatment of ocular hypertension comprising an ophthalmologically acceptable carrier and an effective ocular antihypertensive amount of a compound of claim 1.

7. A method of treating ocular hypertension comprising administering to a patient in need of such treatment an effective ocular antihypertensive amount of a compound of claim 1.

* * * * *